United States Patent [19]

Rizkalla et al.

[11] Patent Number: 5,138,093
[45] Date of Patent: Aug. 11, 1992

[54] PROCESS FOR PREPARING ETHYLIDENE DIACETATE

[75] Inventors: Nabil Rizkalla, River Vale; Charles N. Winnick, Ridgewood, both of N.J.

[73] Assignee: Eastman Kodak Company, Rochester, N.Y.

[21] Appl. No.: 654,662

[22] Filed: Feb. 5, 1976

Related U.S. Application Data

[63] Continuation-in-part of Ser. No. 556,749, Mar. 10, 1975, abandoned.

[51] Int. Cl.⁵ ............... C07C 67/36; C07C 67/37; C07C 69/16

[52] U.S. Cl. .................. 560/232; 562/517; 562/607; 562/891

[58] Field of Search ............. 260/491, 496; 560/232

[56] References Cited

U.S. PATENT DOCUMENTS 3,769,329 10/1973 Paulik et al. ............... 260/491
3,772,380 11/1973 Paulik et al. ............... 260/491

*Primary Examiner*—Vivian Garner

[57] ABSTRACT

Ethylidene diacetate is prepared by treating at least one member of the group consisting of methyl acetate and dimethyl ether with carbon monoxide in the presence of a source of halide under substantially anhydrous conditions.

12 Claims, No Drawings

PROCESS FOR PREPARING ETHYLIDENE DIACETATE

CROSS REFERENCE TO RELATED APPLICATION

This application is a continuation-in-part of co-pending application Ser. No. 556,749, filed Mar. 10, 1975, now abandoned.

BACKGROUND OF THE INVENTION

This invention relates to the preparation of ethylidene diacetate (1,1-diacetoxyethane) by the application of carbonylation techniques to dimethyl ether and/or methyl acetate in the presence of hydrogen.

Ethylidene diacetate is a chemical intermediate of great commercial interest in view of its ready convertibility to a number of different tonnage chemicals of commerce. By one known conversion technique, ethylidene diacetate is readily transformed to vinyl acetate plus acetic acid; see Kirk-Othmer "*Encyclopedia of Chemical Technology,*" (2nd ed.), vol. 21, page 321, Interscience, New York (1970). By another well-known conversion technique, ethylidene diacetate can be transformed into acetic anhydride plus acetaldehyde; see Kirk-Othmer "*Encyclopedia of Chemical Technology,*" (2nd ed.), vol. 8, pages 410–413, Interscience, New York (1965). Reference is also made to U.S. Pat. No. 2,425,389 as indicative of the flexibility of ethylidene diacetate as a chemical intermediate.

Heretofore, however, the potential of ethylidene diacetate as a chemical intermediate has been severely limited by an absence of economic techniques for its preparation from readily available, inexpensive raw materials. One technique for ethylidene diacetate production involves the reaction of acetaldehyde and acetic anhydride to produce ethylidene diacetate as an intermediate for the production of vinyl acetate, a process which has been employed to a limited extent on a commercial scale; see "Hydrocarbon Process." 44 (11), 287 (1965). Another technique has involved the reduction of acetic anhydride with hydrogen; see Fenton, U.S. Pat. No. 3,579,566.

In consequence ethylidene diacetate's potential as a chemical intermediate has not been realized since its manufacture has involved the utilization of quite expensive raw materials which are today in short supply. In further consequence modern chemical technology has focused on the utilization of ethylene as the raw material for the production of acetic anhydride, acetaldehyde, vinyl acetate, and acetic acid. Ethylene production, of course, is contingent upon the use of petroleum fractions which are equally in short supply and not readily producible directly from carbon itself or from methane.

The utilization of non-petroleum based raw materials for the production of materials commercially derived from ethylene, such as the four enumerated above, has been and is today the subject of much research primarily focused upon the employment of carbonylation techniques, i.e., the reaction of carbon monoxide (with or without the concurrent presence of hydrogen) with organic materials. By such carbonylation techniques, a variety of materials have been produced successfully, at least upon a laboratory scale. Much of the early work in this area is summarized in Reppe, "*Acetylene Chemistry,*" PB Report-18852-s, Charles A. Meyer & Co., Inc. (translator), at pages 162 et seq. (1949). However, in none of this early work was there any indication that ethylidene diacetate could be obtained by carbonylation techniques. In later work, in for example, Reppe et al., U.S. Pat. No. 2,727,902, methanol, carbon monoxide, and hydrogen were reacted under carbonylation conditions to yield "acetaldehyde dimethyl acetal," which is more commonly known as ethylidene dimethyl ether; see Merck Index, 8th ed., page 374, Merck & Co., New Jersey (1968). Indeed, acetals are the only gem-type compounds heretofore known as being capable of being produced by carbonylation techniques; see Butter, U.S. Pat. No. 3,285,948, and Schultz, U.S. Pat. No. 3,689,533.

In summary, though much effort has been devoted to research in the area of carbonylation reactions, in no known instance have carbonylation techniques heretofore been disclosed for preparation of ethylidene diacetate despite the obvious desirability of this material as a chemical intermediate.

SUMMARY OF THE INVENTION

In accordance with this invention, it has now been found that ethylidene diacetate can be produced by contacting (a) at least one member of the group consisting of methyl acetate and dimethyl ether, (b) carbon monoxide, and (c) hydrogen with a source of halide within a reaction zone under substantially anhydrous conditions. In this invention the halide is selected from the group consisting of bromide or iodide, or mixtures of bromide and iodide; iodide is preferred.

The process of this invention can be carried out in vapor or liquid phase, with liquid phase operation being preferred. In vapor phase operation the carbon monoxide, hydrogen and methyl acetate (and/or dimethyl ether) together with the source of halide are introduced for contact within the reaction zone. In the liquid phase preferred embodiment, the carbon monoxide, hydrogen and methyl acetate (and/or dimethyl ether) reactants are contacted with a liquid phase reaction medium confined within the reaction zone and maintained in contact therewith for a time sufficient to permit reaction to occur. In this preferred (liquid phase) embodiment, the source of halide can be a component of the liquid phase reaction medium and need not be introduced together with the reactants. A portion of the liquid phase reaction medium, now containing ethylidene diacetate, can then be withdrawn from the reaction zone and processed for the recovery of ethylidene diacetate. The ethylidene diacetate can then be marketed as such or can be converted to acetaldehyde plus acetic anhydride and/or to vinyl acetate plus acetic acid.

The over-all reaction that appears to occur when methyl acetate is employed as the reactant can be expressed by the following chemical equation:

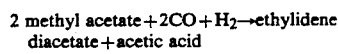
2 methyl acetate + 2CO + H$_2$→ethylidene diacetate + acetic acid

When dimethyl ether is used as the reactant in lieu of methyl acetate, the over-all reaction is slightly different and can be expressed by the following chemical equation:

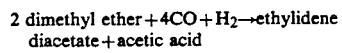
2 dimethyl ether + 4CO + H$_2$→ethylidene diacetate + acetic acid

Mixtures of methyl acetate and dimethyl ether can, of course, be used. Further, although the foregoing equations indicate acetic acid as a primary reaction co-product, other co-products are often obtained instead of or in addition to acetic acid. The other primary co-products often observed are acetic anhydride and/or acetaldehyde. The nature and distribution of these co-products depends in large measure upon the ratio of carbon monoxide to hydrogen employed, as hereinafter discussed. Formation of ethanol or other ethyl derivatives, however, is not noted to occur to a significant extent, though these may be formed in trace amounts.

The mechanism of the reaction or reactions occurring is not known. It is unlikely, however, that the desired ethylidene diacetate is primarily formed by reaction (i.e., reduction) of acetic anhydride with hydrogen present in the system, a reaction disclosed by Fenton in U.S. Pat. No. 3,579,566, because of the behaviour of the reaction system of this invention in the presence of especially preferred catalyst systems. According to recognized reaction mechanism postulates with such preferred catalyst systems (see Khan and Martell, "*Homogeneous Catalysis of Metal Complexes,*" Vol. I, Academic Press, New York (1974) at pages 49 and 315), the formation of organo-metallic complexes of such catalysts with acid anhydrides would be expected to be far less favored than would the formation of such complexes with suspected reaction intermediates such as acyl halides. The ready formation of such complexes with acyl halides leads to facile reduction of the acyl halide in comparison to the acid anhydrides which would tend to preclude involvement of anhydride reduction as a significant factor in the observed ethylidene diacetate formation reaction.

It will be further noted that the acetic acid co-product of the over-all carbonylation reaction is readily recovered as, for example, by distillation techniques, and can be purified for use as such and/or can be reacted with methanol to produce the methyl acetate reactant. Purification of the co-product acetic acid obtained in this process is particularly facile since, because the reaction medium is anhydrous, water removal is not required to achieved concentrations approaching glacial. When the acetic acid is recycled for use in preparing additional methyl acetate, the over-all effect can, in practice, result in a no co-product ethylidene diacetate production process.

Further, since methanol itself can be readily converted to dimethyl ether and/or to methyl acetate by known techniques, the process of this invention provides a facile technique for the conversion of methanol to ethylidene diacetate. And since methanol need not be obtained from petroleum-based materials, the advantages of this process over currently prevailing techniques for production of any one or more of acetic anhydride, acetaldehyde, vinyl acetate, and acetic acid becomes readily apparent.

The reactions described by the foregoing equations are advantageously carried out in the presence of appropriate catalyst systems. Those based upon the Group VIII noble metal catalysts, particularly ones based upon palladium, iridium, and rhodium, most preferably palladium and/or rhodium, are especially advantageous. The efficacy of these preferred noble metal catalyst systems is enhanced, particularly with respect to the reaction rate and concentration of the desired products by the concurrent use of organic promoters capable of forming a coordination compound with the Group VIII noble metals catalyst. Suitable organic promoters are organic non-hydrocarbon materials containing within their molecular structure one or more electron rich atoms possessing one or more pairs of electrons available for formation of coordinate bonds with the noble metal catalyst. Most such organic promoters can be characterized as Lewis bases for the particular anhydrous reaction system involved. Enhancement of catalyst performance is also obtained by the use of inorganic (primarily metallic) promoters in lieu of or in addition to the organic promoters. Suitable metallic promoters include elements and/or compounds of elements having atomic weights greater than 5 of Groups IA, IIA, IIIA, IVB, VIB, the non-noble metals of Group VIII, and the metals of the lanthanide and actinide groups of the Periodic Table as set forth in the "*Handbook of Chemistry and Physics,*" 42nd Ed., Chemical Rubber Publishing Co., Cleveland, Ohio (1960) at pages 448–449. Preferred inorganic promoters include the metals of Groups VIB and the non-noble metals of Group VIII, especially chromium, iron, cobalt, and nickel and most preferably chromium.

Similar catalyst systems are also disclosed for carbonylation reactions in systems wherein hydrogen (though possibly present in but trace amounts) is not a significant reactant in the commonly assigned application of Nabil Rizkalla entitled "Process for Preparing Carboxylic Acid Anhydrides" (attorney docket number 1087A), the disclosure of which is incorporated herein by reference.

The surprising nature of this invention is further illustrated by comparing the carbonylations herein described with those disclosed in Schultz, U.S. Pat. No. 3,689,533. In the Schultz patent catalysts similar to those preferred for use herein are employed, but in water-containing reaction systems; yet ethylidene diacetate is not taught as produced despite the employment of very substantial amounts of hydrogen in conjunction with carbon monoxide in the carbonylation reaction (note especially Example 10 of this reference). It is fundamentally surprising that the conjoint use of a substantially anhydrous reaction system and hydrogen should so profoundly influence the course of the reaction so as to permit the obtaining of a product never heretofore suggested as obtainable by carbonylation techniques.

DETAILED DESCRIPTION OF THE INVENTION

As indicated, this invention provides for the preparation of ethylidene diacetate by the interaction of carbon monoxide and hydrogen with at least one member of the group consisting of dimethyl ether and methyl acetate. This reaction takes place in the vapor or liquid phase, with liquid phase reaction being preferred.

When using dimethyl ether as the organic raw material (in addition, of course, to carbon monoxide and hydrogen), it is believed (but not confirmed) that the initial step involved is the carbonylation of the ether to produce methyl acetate. Thus, although dimethyl ether can readily be employed as a raw material for use in the process of this invention, the use of methyl acetate (alone or in admixture with dimethyl ether) is particularly preferred.

When dimethyl ether is employed as the starting material for the process of this invention, the reaction can be carried out in one or more reaction zones. Thus, in this embodiment, a preferred procedure would involve the use of two reaction zones, in the first of which dimethyl ether would be converted by carbonylation to methyl acetate, with the second reaction zone being devoted to the conduct of the ethylidene diacetate-forming reaction. In this fashion differing reaction conditions can be employed for (a) the conversion of dimethyl ether to methyl acetate and (b) the conversion of methyl acetate to ethylidene diacetate so that each of the two reaction zones may be maintained under optimum conditions for the reactions conducted therein.

However, the use of separate reaction zones is not necessary because the conversion of dimethyl ether to methyl acetate can be carried out concurrently with and in the same reaction zone as that in which the ethylidene diacetate is formed.

Aside from the dimethyl ether and/or methyl acetate reactants, necessary reactants for the production of the ethylidene product are carbon monoxide and hydrogen. These can be introduced to the reaction zone (or zones) either together or separately. In vapor phase operation, it is, of course, also necessary to introduce the source of halide together with the reactants, again either together with or separately from the reactants.

It will be noted that while hydrogen is a necessary co-reactant with carbon monoxide for the production of ethylidene diacetate, it is not a necessary co-reactant for the conversion of dimethyl ether to methyl acetate. Assuming for convenience that carbon monoxide and hydrogen are separately introduced to the reaction zone wherein ethylidene diacetate is produced, each is preferably employed in substantially pure form, as available commercially. In each case, however, inert diluents such as carbon dioxide, nitrogen, methane, and/or inert gases (e.g., helium, argon, neon, etc.) can be present if desired. The presence of inert diluents of these types does not affect the desired carbonylation reactions, but their presence makes it necessary to increase the total pressure in order to maintain the desired carbon monoxide and hydrogen partial pressures.

All reactants (i.e., carbon monoxide, hydrogen, as well as the methyl acetate and/or dimethyl ether) should be substantially free from water since, in this fashion, the maintenance of a substantially anhydrous condition within the reaction zone is facilitated. The presence of minor amounts of water, however, such as may be found in these commercially available reactants, is permissible. Normally, however, the presence of more than 5 mole % of water in any one or more of the reactants should be avoided, the presence of less than 3 mole % of water is desired, and the presence of less than 1.0 mole % of water is preferred. More important, however, than the amount of water in feed or recycle streams introduced to the reaction zone is the concentration of free water plus alcoholic hydroxyl groups (which react in situ to form water) present within the reaction zone. In practice, the molar ratio of (a) water plus the molar equivalents of alcoholic hydroxyl groups to (b) the number of moles of dimethyl ether and/or methyl acetate within the reaction zone is the most convenient method for defining this concentration. On this basis, this ratio preferably should not exceed 0.1:1. Still lower values for this ratio are advantageous, with optimal results being obtained with values for this ratio ranging from about zero to about 0.05:1. In vapor phase operation, control of this ratio is readily accomplished by appropriate adjustment of the water and/or free alcohol (e.g., methanol) content of all streams introduced to the reaction zone in relation to the quantity of ether and/or ester reactant introduced thereto. In the preferred liquid phase operation, control of this ratio is readily accomplished by maintaining the liquid phase reaction medium with the reaction zone in a substantially anhydrous state.

The presence of the conventional organic impurities found in commercial grades of dimethyl ether and/or methyl acetate, however, pose no problem to the practice of this invention.

As hereinabove indicated, preferred practice calls for conduct of the instant reaction in the liquid phase in the presence of a substantially anhydrous liquid phase reaction medium. Since water is not a product of the reaction, maintenance of substantially anhydrous conditions within the liquid phase reaction medium is simply accomplished by insuring adequate dryness and freedom from alcoholic hydroxyl groups (i.e., free alcohol) of the necessary reactants and/or recycle streams (hereinafter discussed) introduced to the reaction zone. The liquid phase reaction medium thus contains reactants (carbon monoxide, hydrogen, dimethyl ether, and/or methyl acetate), reaction products (ethylidene diacetate, and acetic acid), as well as the halide necessary for the conduct of the desired reaction, together with such co-products as may be formed, including usually acetaldehyde and/or acetic anhydride.

To facilitate conduct of the reaction in the liquid phase, solvents or diluents can be employed. The solvents or diluents are preferably materials which are indigenous to the reaction system such as, for example, excess dimethyl ether and methyl acetate and/or methyl halide and/or acetyl halide (preferred halide sources), and/or co-products commonly found in the reaction system, such as acetic acid, acetaldehyde, and/or acetic anhydride. Excess dimethyl ether and/or methyl acetate are the preferred reaction diluents, with acetic acid and/or acetic anhydride being the preferred alternates.

It is also practicable to employ organic solvents or diluents which are inert in the enviroment of the process. The most suitable inert solvents or diluents are hydrocarbons free from olefinic unsaturation, typically the paraffinic, cycloparaffinic, and aromatic hydrocarbons such as octane, benzene, toluene, the xylenes, cyclododecane, and the like. Other suitable solvents include chloroform, carbon tetrachloride, and acetone. When such non-indigenous solvents or diluents are employed, they are preferably selected so that the solvent or diluent has a boiling point sufficiently different from the components of the reaction mixture to facilitate the separation of the components of the reaction mixture from the solvent or diluent.

Also as hereinbefore indicated, the reaction requires the presence of a halide which, in the preferred liquid phase mode of operation, would be a component of the liquid phase reaction medium. Suitable halides are either bromide or iodide or mixtures thereof, iodide being preferred. The halide would usually be present largely in the form of methyl halide, acetyl halide, hydrogen halide, or mixtures of the foregoing species, and could be introduced to the liquid phase reaction medium as such. However, it is entirely sufficient, particularly in batch operation, to charge materials to the liquid phase such that any one or more of these materials (i.e., methyl halide, acetyl halide, and/or hydrogen halide) are formed in situ. Materials which interact in situ with the other components of the liquid phase reaction medium to form methyl halide, acetyl halide, and/or hydrogen halide include inorganic halide materials, e.g., salts such as the alkali metal and alkaline earth metal salts, as well as elemental iodine and bromine. In continuous operation, wherein reaction by-products are separated (as for example, by distillation and/or extraction techniques), and recycled to the reaction medium, organic halides such as methyl halide and/or acetyl halide will be present as components of the liquid phase reaction medium and can be recovered and recycled to the reaction zone as such; thus, only a small quantity of make-up halide need be supplied to compensate for such losses in recovery as may be encountered.

The amount of halide that should be present in the liquid phase reaction medium is related to the amount of ether and/or ester reactant introduced to the reaction zone, but otherwise can vary over a wide range. Typically 0.5 to 1,000 moles of ester or ether per equivalent of halide, desirably 1 to 300 moles per equivalent, and preferably 2 to 100 moles per equivalent are used. In general, higher proportions of halide to ether and/or ester reactant tend to increase reaction rate.

In typical practice the liquid phase reaction medium, neglecting water and non-indigenous solvents or diluents employed, would normally contain the following materials within the following concentration ranges, expressed on a mole % basis unless otherwise indicated:

Halide, wt. % (contained basis): 0.1–75%
Acetaldehyde: 0–40%
Acetic acid: 1–75%
Acetic anhydride: 0–80%
Ethylidene diacetate: 1–60%
Dimethyl ether: 0–50%
Methyl acetate: 5–90%

When non-indigenous solvents are employed, they would normally comprise from 5 wt. % to 95 wt. %, desirably from 10 wt. % to 90 wt. %, and preferably from 15 wt. % to 80 wt. % of the liquid phase reaction medium.

Also not included in the foregoing tabulation are the quantities of dissolved carbon monoxide and hydrogen necessarily present within the liquid phase reaction medium in order to permit the desired reaction or reactions to occur.

It will be noted that liquid phase reaction media within the foregoing concentration ranges are readily processible in order to recover ethylidene diacetate therefrom because of the wide difference in volatilities associated with these materials. Methyl halides are generally highly volatile materials. These can thus be readily separated by distillation and/or extraction techniques for recovery and recycle to the reaction zone. Any acetic acid and acetic anhydride present in the system can readily be recovered. Ethylidene diacetate, however, is of substantially lesser volatility and can accordingly readily be recovered in whatever degree of purity may be desired. Inert solvents or diluents, if present, can readily be chosen from the standpoint of volatility characteristics to facilitate their recovery and re-use.

As indicated, the process of this invention preferably occurs in the presence of a liquid phase reaction medium confined within a reaction zone. A single reaction zone or a plurality of reaction zones in series or in parallel may be employed. The process itself can be carried out in batch, semi-continuous, or continuous manner. The reaction zone itself may comprise one or more autoclaves or an elongated tubular zone or series of such zones. Of course, reaction zone construction should be such that the reaction zone can withstand reaction temperature and pressure and should be fabricated from materials inert during the conduct of the reaction. Suitable inert materials for reaction zone construction include tantalum, zirconium, various of the stainless steels, the Hastelloys, and the like. The reaction zone is suitably fitted with internal and/or external heat-removal devices to absorb the exothermic heat of reaction and facilitate maintenance of proper temperature control during the course of the reaction. Suitably, the reaction zone is configured to provide sufficient agitation to insure adequate contact between the carbon monoxide and hydrogen reactants and the ether-acetate reactants. Any convenient agitation means known to those skilled in the art may be used, including vibration, shaking, stirring, etc., as illustrative techniques. Normally the reactants would be introduced at a point within the reaction zone below the level of the liquid phase reaction medium maintained therewithin in order to facilitate agitation and adequate contact by gas-sparging techniques.

The process of this invention can be carried out over a wide range of temperatures. Temperatures, for example from 20°–500° C. are suitable, with temperatures of 80°–350° C. being desired, and temperatures of 100°–250° C. being preferred. Temperatures lower than those mentioned can be used but they tend to lead to reduced reaction rates. Higher temperatures than those mentioned can be employed, but there is no particular advantage to such practice.

Reaction time is not a significant parameter of the process of this invention, depending to a large extent upon the temperature employed as well as upon reactant concentrations. Suitable reaction times (i.e., times sufficient for the ethylidene diacetate-forming reaction to occur) for liquid phase embodiments will normally be within the range of 0.05 to 20 hours. Reaction time in a batch system is self-explanatory. In a continuous system, the residence time is defined as the quotient obtained by dividing the volume of the liquid phase reaction medium within the reaction zone by the rate (in consistent volume units per hour) at which the dimethyl ether and/or methyl acetate (both fresh feed and any recycled material) is introduced to the reaction zone.

For the preferred liquid phase emobdiments, reaction total pressure also is an unimportant process parameter so long as it is sufficient to maintain the liquid phase reaction medium and the appropriate carbon monoxide and hydrogen partial pressures. Suitable carbon monoxide and hydrogen partial pressures are each preferably within the range of 5–5,000 psi, most preferably within the range of 25–3,000 psi. Broader partial pressure ranges, however, can be employed, with ranges from 0.1 to 15,000 psi being applicable. While yet higher partial pressures can be employed, there is little advantage to their use and a substantial economic penalty would be incurred as a result of building equipment capable of withstanding such higher pressures.

The stoichiometry of the chemical equations presented earlier in this specification suggests that the reaction resulting in the formation of ethylidene diacetate would require a molar ratio of carbon monoxide to hydrogen varying from 2:1 to 4:1, depending upon whether dimethyl ether or methyl acetate (or mixtures thereof) was employed. It has, however, been found that much broader molar ratios of carbon monoxide to hydrogen, broadly within the range of 1:100 to 100:1, desirably within the range of 50:1 to 1:50, and preferably within the range of 10:1 to 1:10 can be employed. Best results are obtained with carbon monoxide-hydrogen mixtures which approach the stoichiometric ratios of carbon monoxide to hydrogen. Molar ratios of carbon monoxide to hydrogen within the range of 0.5:1 to 5:1 are thus an especially preferred regime of operation.

The molar ratios of carbon monoxide to hydrogen also affects the nature of the co-products obtained. The foregoing equations indicate that acetic acid is the co-product formed. Other co-products can however be made, especially acetic anhydride and acetaldehyde. For example, other conditions remaining constant in a liquid phase system, increasing the molar ratio of carbon monoxide to hydrogen increases the molar ratio of acetic anhydride to acetic acid produced. Conversely, reducing the molar ratio of carbon monoxide to hydrogen increases the molar ratio of acetaldehyde to acetic acid produced. Thus, the process of this invention provides a considerable degree of flexibility in the distribution of co-products obtainable.

For liquid phase operation, the molar ratios of carbon monoxide plus hydrogen to dimethyl ether and/or methyl acetate employed are dictated by the partial pressure criteria set forth above, since partial pressure and liquid phase concentration of these normally gaseous reactants are directly interrelated.

Once the reaction has been carried out, the reaction effluent is withdrawn from the reaction zone and introduced into a distillation zone which can comprise one or a series of distillation columns. In these columns, ethylidene diacetate and co-product acetic acid (and/or acetic anhydride and/or acetaldehyde) are recovered and unconverted or partially converted materials and halogen-containing components of the reaction medium are recovered for recycle to the reaction zone. The catalyst can also be readily recovered for recycle to the reaction zone if desired.

As hereinbefore indicated, the ethylidene diacetate-forming reaction to which this invention is directed is advantageously carried out in the presence of a carbonylation catalyst. In preferred practice, this carbonylation catalyst employed is based upon the use of one or more Group VIII noble metal catalysts, i.e., one or more of ruthenium, rhodium, palladium, osmium, iridium, platinum. Those based upon palladium, iridium, and rhodium are preferred, while rhodium and/or palladium appear to be especially advantageous and are particularly preferred.

The carbonylation catalyst, suitably a Group VIII noble metal, can be employed in any convenient form, viz., in the zero valent state or in any higher valent form. For example, the catalyst to be added can be the metal itself, in finely divided form, or it can be added as a carbonate, oxide, hydroxide, nitrate, bromide, iodide, chloride, lower alkoxide (i.e., $C_1$–$C_5$, such as the methoxide or ethoxide), phenoxide, or metal carboxylate wherein the carboxylate ion is derived from an alkanoic acid of 1 to 20 carbon atoms. Similarly, complexes of the metals can be employed, for example, the metal carbonyls, such as the iridium and rhodium carbonyls, or as other complexes such as the carbonyl halides, e.g., iridium tri-carbonyl chloride $[Ir(CO)_3Cl]_2$ or as the acetylacetonates, e.g., rhodium acetylacetonate, $Rh(C_5H_7O_2)_3$. Pre-formed ligand-like complexes can also be employed, such as dichloro bis-(triphenylphosphine) palladium, dichloro bis-(triphenylphosphine) rhodium, and trichloro tris-pyridene rhodium. Using rhodium as illustrative of the preferred noble metal carbonylation catalysts, illustrative forms in which the noble metal carbonylation catalyst can be added to the system include, aside from those already specifically listed, rhodium oxide ($Rh_2O_3$), tetrarhodium dodecacarbonyl, dirhodium octacarbonyl, hexarhodium hexadecacarbonyl ($Rh_6(CO)_{16}$), rhodium (II) formate, rhodium (II) acetate, rhodium (II) propionate, rhodium (II) butyrate, rhodium (II) valerate, rhodium (III) naphthenate, rhodium dicarbonyl acetylacetonate, rhodium trihydroxide, indenylrhodium dicarbonyl, rhodium dicarbonyl (1-phenylbutane-1,3-dione), tris(hexane-2,4-dione) rhodium (III), tris(heptane-2,4-dione) rhodium (III), tris(1-phenylbutane-1,3-dione) rhodium (III), tris(3-methylpentane-2,4-dione) rhodium (III), and tris(1-cyclohexylbutane-1,3-dione) rhodium (III).

For liquid phase reaction systems, the noble metal catalyst can be employed in forms initially or eventually soluble in the liquid phase reaction medium to provide a homogeneous catalyst system. Alternatively, insoluble (or only partially soluble) forms, providing a heterogeneous catalyst system, can be employed. Amounts of carbonylation catalyst (calculated as contained noble metal based upon the total quantity of liquid phase reaction medium) of as little as about $1 \times 10^{-4}$ wt. % (1 ppm) are effective, although normally amounts of at least 10 ppm, desirably at least 25 ppm, and preferably at least 50 ppm would be employed. Upper concentration limit on carbonylation catalyst quantity appears to be controlled more by economics than by any advantage in either rate or selectivity that can be observed. These limits would normally suggest that more than 50,000 ppm of contained noble metal would not normally be employed. An optimum balancing of reaction rate and economic criteria would normally suggest the use of amounts of contained noble metal carbonylation catalyst based upon the total weight of liquid phase reaction medium between about 10 and about 50,000 ppm, desirably between about 100 and 25,000 ppm, and preferably between about 500 and 10,000 ppm.

The efficacy of these preferred noble metal catalyst systems, as has been noted above, is enhanced, particularly with respect to the reaction rate and concentration of the desired products, by the concurrent use of promoters. Effective promoters can be inorganic or organic or can be mixtures (or compounds) of both organic and inorganic species.

Suitable organic promoters are non-hydrocarbon materials capable of forming a coordination compound with the Group VIII noble metal catalyst, containing within their molecular structure one or more pairs of electrons available for formation of coordinate bonds with the noble metal catalyst. Such promoters can be introduced concurrently with the reactants to the reaction zone or can be incorporated together with the Group VIII noble metal by formation of ligand complexes with the noble metal prior to introduction of the noble metal-ligand complex to the reaction zone. When pre-formed ligand complexes are used, concurrent use of promoters (either organic or inorganic) is not necessary, though of course such can be employed if desired.

Suitable organic promoters are organo-phosphine, organo-arsine, organo-stibine, organo-nitrogen, and organo-oxygen containing compounds. Organo-phosphine and organo-nitrogen promoters are preferred classes.

Suitable oxygen-containing compounds capable of functioning as organic promoters in this system are those containing functional groups such as the phenolic hydroxyl, carboxyl, carbonyloxy, carbonyl, and the like groups. Suitable organo-nitrogen containing compounds are those containing amino, imino, and nitrilo groups. Materials containing both oxygen and nitrogen atoms can be used.

Illustrative oxygen-containing organic promoters, by way of illustration but not limitation, are glycolic acid, methoxyacetic acid, ethoxyacetic acid, diglycolic acid, thiodiglycolic acid, benzoic acid, pyromellitic acid, toluic acid, tetrahydrofuran, dioxane, tetrahydropyran, pyrocatechol, citric acid, 2-methoxyethanol, 2-ethoxyethanol, 2-n-propoxyethanol, 2-n-butylethanol, 1,2,3-trihydroxybenzene, 1,2,4-trihydroxybenzene, 2,3-dihydroxynaphthalene, cyclohexane-1,2-diol, 1,3-epoxypropane, 1,2-dimethoxybenzene, 1,2-diethoxybenzene, 1,2-dimethoxyethane, 1,2-diethoxyethane, 1,2-di-n-propoxyethane, 1,2-di-n-butoxyethane, pentane-2,4-dione, hexane-2,4-dione, heptane-3,5-dione, octane-2,4-dione, 1-phenylbutane-1,3-dione, 3-methylpentane-2,4-dione; the mono- and dialkyl ethers of propylene glycol, of diethylene glycol, of dipropylene glycol; and the like.

Suitable nitrogen-containing organic promoters include, by way of illustration, pyrrole, pyrrolidine, pyridine, piperidine, pyrimidine, the picolines, pyrazine (and their N-lower-alkyl-substituted derivatives, lower alkyl meaning $C_1$-$C_5$ such as N-methyl pyrrolidine), benzotriazole; N,N,N',N'-tetramethylethylenediamine, N,N,N',N'-tetraethylethylenediamine, N,N,N',N'-tetra-n-propylethylenediamine, N,N,N',N'-tetramethylmethylenediamine, N,N,N',N'-tetraethylmethylenediamine, N,N,N',N'-tetraisobutylmethylenediamine, piperazine, N-methylpiperazine, N-ethylpiperazine, 2-methyl-N-methylpiperazine 2,2'-dipyridyl, methyl-substituted 2,2'-dipyridyl, ethyl-substituted 2,2'-dipyridyl, 1,4-diazabicyclo[2.2.2] octane, methyl-substituted 1,4-diazabicyclo[2.2.2] octane, purine, 2-aminopyridine, 2-(dimethylamino)pyridine, 1,10-phenanthroline, methyl-substituted 1,10-phenanthroline, 2-(dimethylamino)-6-methoxyquinoline, 7-chloro-1,10-phenanthroline, 4-triethylsilyl-2,2'-dipyridyl, 5(thiapentyl)-1,10-phenanthroline, tri-n-butylamine, and the like.

Suitable organic promoters containing both oxygen and nitrogen atoms are ethanolamine, diethanolamine, isopropanolamine, di-n-propanolamine, N,N-dimethylglycine, N,N-diethylglycine, 1-methyl-2-pyrrolidinone, 4-methylmorpholine, N,N,N',N'-tetramethylurea, iminodiacetic acid, N-methyliminodiacetic acid, N-methyldiethanolamine, 2-hydroxypyridine, methyl-substituted 2-hydroxypyridine, picolinic acid, methyl-substituted picolinic acid, nitrilotriacetic acid, 2,5-dicarboxypiperazine, N-(2-hydroxyethyl)iminodiacetic acid, ethylenediaminetetraacetic acid, 2,6-dicarboxypyridine, 8-hydroxyquinoline, 2-carboxyquinoline, cyclohexane-1,2-diamine-N,N,N',N'-tetraacetic acid, the tetramethyl ester of ethylenediaminetetraacetic acid, and the like.

Suitable stibines and arsines are exemplified by the following illustrative materials: trimethyl arsine, triethyl arsine, triisopropyl stibine, ethyldiisopropyl stibine, tricyclohexyl arsine, triphenyl stibine, tri(o-tolyl)-stibine, phenyldiisopropyl arsine, phenyl diamyl stibine, diphenylethylarsine, tris(diethylaminomethyl) stibine, ethylene bis(diphenyl arsine), hexamethylene bis(diisopropyl arsine) pentamethylene bis(diethylstibine) etc.

Preferred organic promoters are the organo nitrogen or organo phosphorus compounds wherein the nitrogen or phosphorus atoms are, at least in part, trivalent. Many of these preferred compounds may also contain oxygen atoms such as, for example, 1-methyl-2-pyrrolidinone and N,N,N',N'-tetramethylurea. Especially preferred are the tertiary amines of the formula:

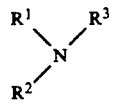

wherein $R^1$, $R^2$, and $R^3$ are the same or different and are alkyl, cycloalkyl, or aryl radicals, each preferably having not more than about 10 carbon atoms. Also especially preferred are the heterocyclic amines of the pyridine type such as pyridine itself, the picolines, quinoline, and methyl quinoline. The tertiary phosphines of the following formula:

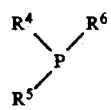

wherein $R^4$, $R^5$, and $R^6$ have the same meaning as $R^1$, $R^2$, and $R^3$, respectively, are also especially preferred. Exemplary of particularly suitable phosphines include trimethyl phosphine, tri-t-butyl phosphine, tri-n-butyl phosphine, tricyclohexyl phosphine, and triphenyl phosphine.

The quantity of organic promoter employed is related to the quantity of noble metal catalyst within the reaction zone. Normally the quantity is such that at least 0.1, desirably at least 0.2, and preferably at least 0.3 mole of promoter compound per mole of noble metal is present in the reaction zone. Little advantage is observed, on the other hand, when large excesses of organic promoter per mole of noble metal catalyst are employed. Normally, therefore, operation with more than 500 moles of promoter per mole of noble metal catalyst in the reaction zone would not be employed. Desirably less than 200 moles of promoter per mole of noble metal, and preferably less than 100 moles of promoter per mole of noble metal catalyst would be used. Particularly advantageous results are obtained when the number of moles of organic promoter per mole of noble metal catalyst within the reaction zone is between 0.2 and 200 moles per mole, and preferably between 0.3 to 100 moles per mole.

The foregoing ratios of organic promoter to noble metal of course assume that the promoter and noble metal are introduced to the reaction zone as distinct species. When, as also indicated to be practicable, preformed organic promoter-noble metal ligand complexes are employed, the amount of promoter is, of course, dictated by the stoichiometry of the complex. Additional promoter can then be added to the reaction zone during the course of the reaction, either periodically or continuously, to assist in maintenance of the stability of the complex, if desired.

An additional type of organically promoted noble metal catalysts of utility as carbonylation catalysts for the process of this invention are those in which the noble metal catalyst metal is chemically bonded to a polymeric substrate which can be organic or inorganic. Such metal-polymer complexes are clearly heterogeneous in the physical sense because insoluble; however, they display chemical characteristics more nearly akin to homogeneous than to heterogeneous catalysis. Such metal-polymer complexes and procedures for their preparation are known; see Michalska, Z. M. and Webster, D.E. "Supported Homogeneous Catalyst,"

*CHEMTECH*, Feb. 1975, pages 117–122 and references cited therein. Those complexes particularly suitable for use in this invention comprise noble metal bonded to a silica, polyvinyl chloride or cross-linked polystyrene-divinylbenzene substrate by phosphine, silyl, amine, or sulfide linkages.

Effective inorganic promoters include the elements (and compounds of elements) having atomic weights greater than 5 of Groups IA, IIA, IIIA, IVB, VIB, the non-noble metals of Groups VIII, and the metals of the lanthanide and actinide groups of the Periodic Table. Particularly preferred are the lower atomic weight metals of each of these groups, e.g., those having atomic weights lower than 100, and especially preferred are the metals of Group VIB and the non-noble metals of Group VIII. In general, the most preferred elements are lithium, magnesium, calcium, titanium, chromium, cobalt, iron nickel, and aluminum. Most preferred are lithium, chromium, cobalt, iron and nickel, especially chromium.

The inorganic promoters can be used in their elemental form, e.g., as finely divided or powdered metals, or they can be employed as compounds of various types, both organic and inorganic, which are effective to introduce the element as the cation into the reaction system under reaction conditions. Thus, typical compounds of the promoter elements include oxides, hydroxides, halides (preferably bromides and iodides), oxyhalides, hydrides, carbonyls, alkoxides, nitrates, nitrites, phosphates, phosphites, and the like. Especially preferred organic compounds are the salts of organic aliphatic, cycloaliphatic, naphthenic and araliphatic monocarboxylic acids, e.g., alkanoates such as the acetates, butyrates, decanoates, laurates, stearates, benzoates, and the like. Other suitable compounds include the metal alkyls as well as chelates, associate compounds and enol salts. Particularly preferred are the elemental forms, compounds which are bromides and iodides and organic acid salts, preferably acetates. Mixtures of inorganic promoters can be used if desired, especially mixtures of elements from different groups of the Periodic Table.

The quantity of inorganic promoter can vary widely, but preferably it is used in an amount such that from 0.0001 mole to 100 moles per mole of Group VIII noble metal catalyst, most preferably from 0.1 to 10 moles per mole of catalyst, are contained within the reaction zone.

Of course, it is also practicable, and sometimes advantageous, to use both organic and inorganic promoters in conjunction with the noble metal catalyst. Thus, for example (in conjunction with the especially preferred palladium and rhodium noble metal catalysts) systems which are only organic such as, for example, the tertiary amines, heterocyclic nitrogen compounds of the pyridine type, or tertiary phosphines can be employed as the promoters. Inorganic promoters, especially chromium, iron, nickel, or cobalt, and most preferably chromium, can be used instead of the organic types. However, the use of phosphine or amine promoters in conjunction with chromium, iron, nickel, or cobalt, and most preferably with chromium, is practicable and is highly effective.

The following examples are presented to illustrate further the above-described invention but are not intended as limiting the scope thereof. Unless otherwise indicated, all parts and percents in the following examples are on a weight basis. In these examples, the term "liquid phase" means the liquid portion of the reaction mixture other than dissolved catalyst components (including the halide source) which may be present, and other than any solvent used.

EXAMPLE I

To a one gallon autoclave fitted with a turbine-type agitator are charged 60 parts of methyl acetate, 1 part of rhodium chloride trihydrate, 3 parts of 3-picoline, and 20 parts of methyl iodide. The autoclave is then sealed and pressured to 500 psig with carbon monoxide. At this point hydrogen is added to the autoclave, raising the pressure therewithin to 1,000 psig. The autoclave and its contents are then heated to 150° C. and maintained at this temperature for 3 hours, following which the autoclave is allowed to cool, depressured, and the liquid phase therewithin is analyzed by gas chromotographic (G. C.) techniques. The liquid phase is found to contain 44 wt. % ethylidene diacetate, 6.5 wt. % acetic anhydride, and 0.6 wt. % of acetaldehyde, together with a substantial amount of acetic acid. The remainder of the liquid phase is primarily unconverted components of the initial charge.

EXAMPLE II

The procedure and equipment of Example I are employed using as initial charge 60 parts of methyl acetate, 1.6 parts of palladium acetate, 10 parts of triphenyl phosphine, and 20 parts of methyl iodide. Carbon monoxide and hydrogen are added in the same fashion and to the same pressure used in Example I. Reaction is continued for 17 hours at 135° C. Analysis of the reaction products by G. C. tehcniques indicates the reaction effluent to contain 34 wt. % ethylidene diacetate and 5.3 wt. % acetaldehyde, together with a substantial amount of acetic acid. The remainder of the liquid phase is primarily unconverted components of the initial charge.

EXAMPLE III

The procedure and equipment of Example I are employed using as initial charge 60 parts methyl acetate, 5 parts dichloro bis-(triphenylphosphine)palladium, 2 parts triphenylphosphine, and 20 parts methyl iodide. Carbon monoxide and hydrogen are added in the same fashion and to the same pressure used in Example I. Reaction is continued for 17 hours at 135° C. Analysis of the reaction products by G. C. techniques indicates the reaction effluent to contain 31 wt. % ethylidene diacetate and 9.6 wt. % acetaldehyde, together with a substantial amount of acetic acid. The remainder of the liquid phase is primarily unconverted components of the initial charge.

EXAMPLE IV

The procedure and equipment of Example I are employed using as initial charge 60 parts methyl acetate, 1 part rhodium chloride trihydrate, 3 parts chromium carbonyl, and 20 parts methyl iodide. Carbon monoxide and hydrogen are added in the same fashion and to the same pressure used in Example I. Reaction is continued for 4 hours at 150° C. Analysis of the reaction products by G. C. techniques indicates the reaction effluent to contain 13 wt. % ethylidene diacetate, 0.6 wt. % acetaldehyde, and 17.8 wt. % acetic anhydride, together with a substantial amount of acetic acid. The remainder of the liquid phase is primarily unconverted components of the initial charge.

EXAMPLE V

The procedure and equipment of Example I are employed using as initial charge 60 parts methyl acetate, 1 part rhodium chloride trihydrate, and 20 parts methyl iodide. Carbon monoxide and hydrogen are added in the same fashion and to the same pressure used in Example I. Reaction is continued for 3 hours at 150° C. G. C. analysis of the reaction effluent indicated no reaction products to have been obtained. Thus, this example illustrates the advantages accruing to the conjoint use of an organic and/or inorganic promoter together with a noble metal catalyst, as in the preceding examples.

EXAMPLE VI

The procedure and equipment of Example I are employed using as initial charge 60 parts methyl acetate, 2 parts dichloro bis-(triphenylphosphine) rhodium, 3 parts triphenylphosphine, and 20 parts methyl iodide. Carbon monoxide and hydrogen are added in the same fashion and to the same pressure used in Example I. Reaction is continued for 3 hours at 150° C. Analysis of the reaction products by G. C. techniques indicates the reaction effluent to contain 13 wt. % ethylidene diacetate and 7.4 wt. % acetaldehyde, together with a substantial amount of acetic acid. The remainder of the liquid phase is primarily unconverted components of the initial charge.

EXAMPLE VII

The procedure and equipment of Example I are employed using as initial charge 60 parts methyl acetate, 1 part palladium chloride, 3 parts chromium carbonyl, 3 parts of 3-picoline, and 20 parts of methyl iodide. Carbon monoxide and hydrogen are added in the same fashion and to the same pressure used in Example I. Reaction is continued for 3.5 hours at 150° C. Analysis of the reaction products by G. C. techniques indicates the reaction effluent to contain 2 wt. % ethylidene diacetate and 7 wt. % acetaldehyde, together with a substantial amount of acetic acid. The remainder of the liquid phase is primarily unconverted components of the initial charge. This experiment was repeated but the reaction was continued for only 2 hours. G.C. analysis of the liquid phase shows it to contain 10 wt. % ethylidene diacetate and 10 wt. % acetaldehyde with the remainder again being a substantial amount of acetic acid and unconverted components of the initial charge, no acetic anhydride being present.

EXAMPLE VIII

The procedure and equipment of Example I are employed using as initial charge 60 parts methyl acetate, 1.2 parts palladium chloride, and 20 parts methyl iodide. Carbon monoxide and hydrogen are added in the same fashion and to the same pressure used in Example I. Reaction is continued for 17 hours at 135° C. G.C. analysis of the reaction effluent indicated no reaction products to have been obtained. Thus, this example, like Example V, illustrates the advantages accruing to the conjoint use of an organic and/or inorganic promoter together with a noble metal catalyst.

EXAMPLE IX

The procedure and equipment of Example I are employed using as initial charge 60 parts methyl acetate, 2 parts trichloro tris(pyridine) rhodium, and 20 parts methyl iodide. Carbon monoxide and hydrogen are are added in the same fashion and to the same pressure used in Example I. Reaction is continued for 3 hours at 155° C. Analysis of the reaction products by G.C. techniques indicates the reaction effluent to contain 25 wt. % ethylidene diacetate and 42 wt. % acetic anhydride together with a substantial amount of acetic acid. The remainder of the liquid phase is primarily unconverted components of the initial charge. No acetaldehyde is found.

EXAMPLE X

The procedure and equipment of Example I are employed using as initial charge 60 parts methyl acetate, 1.3 parts palladium chloride, 6 parts tri-n-butyl phosphine, and 20 parts methyl iodide. Carbon monoxide and hydrogen are added as in Example I except that the pressures used are 300 and 600 psig, respectively. Reaction is continued for 17 hours at 135° C. Analysis of the reaction products by G.C. techniques indicates the reaction effluent to contain 12.4 wt. % ethylidene diacetate and 12 wt. % acetaldehyde, together with a substantial amount of acetic acid. The remainder of the liquid phase is primarily unconverted components of the initial charge.

EXAMPLE XI

The procedure and equipment of Example I are employed using as initial charge 100 parts (mole basis) of methyl acetate, 17 parts (mole basis) of methyl iodide, and 0.4 part (mole basis) of a pre-formed rhodium pyridine ligand complex having the formula $RhCl_3(pyridine)_3$. Carbon monoxide and hydrogen are added in the same fashion and to the same pressures used in Example I. Reaction is continued for 17 hours at 150° C. Analysis of the reaction products by G.C. techniques indicates the reaction effluent to contain 13 mole % ethylidene diacetate, no acetaldehyde, and no acetic anhydride. The effluent contains a substantial amount of acetic acid, with the remainder of the liquid phase being primarily unconverted components of the initial charge. This example illustrates the employment of a pre-formed noble metal ligand complex in lieu of employment of an organic promoter added as such.

EXAMPLE XII

The procedure and equipment of Example I are employed using as initial charge 60 parts of methyl acetate, 1.6 parts of palladium diacetate, 10 parts of triphenyl phosphine, and 20 parts of methyl bromide. Carbon monoxide and hydrogen are added as in Example I except that the pressures used are 300 and 600 psig, respectively. Reaction is continued for 17 hours at 135° C. Analysis of the reaction products by G. C. techniques indicates the reaction effluent to contain 14 wt. % ethylidene diacetate, 0.4 wt. % acetaldehyde, and 2 wt. % acetic anhydride, together with a substantial amount of acetic acid. The remainder of the liquid phase is primarily unconverted components of the initial charge.

EXAMPLE XIII

The procedure and equipment of Example I are employed using as initial charge 60 parts of methyl acetate, 1.6 parts of palladium diacetate, 2 parts of imidazole, and 20 parts of methyl iodide. Carbon monoxide and hydrogen are added as in Example I except that the pressures used are 300 and 600 psig, respectively. Reaction is continued for 17 hours at 135° C. Analysis of the reaction products by G. C. techniques indicates the reaction effluent to contain 3.4 wt. % ethylidene diacetate and 6.1 wt. % acetaldehyde, together with a substantial amount of acetic acid. The remainder of the liquid phase is primarily unconverted components of the initial charge.

EXAMPLE XIV

The procedure and equipment of Example I are employed using as initial charge 60 parts of methyl acetate, 1.6 parts of palladium diacetate, 3 parts of chromium carbonyl, 15 parts of N,N-dimethyl acetamide, and 20 parts of methyl iodide. Carbon monoxide and hydrogen are added in the same fashion and to the same pressure used in Example I. Reaction is continued for 17 hours at 135° C. Analysis of the reaction products by G.C. techniques indicates the reaction effluent to contain 27 wt. % ethylidene diacetate and 3.3 wt. % acetaldehyde, together with a substantial amount of acetic acid. The remainder of the liquid phase is primarily unconverted components of the initial charge.

EXAMPLE XV

The procedure and equipment of Example I are employed using as initial charge 60 parts of methyl acetate, 1.6 parts of palladium diacetate, 10 parts of hexamethylphosphoramide, and 20 parts of methyl iodide. Carbon monoxide and hydrogen are added in the same fashion and to the same pressure used in Example I. Reaction is continued for 17 hours at 135° C. Analysis of the reaction products by G.C. techniques indicates the reaction effluent to contain 21.7 wt. % ethylidene diacetate and 1.6 wt. % acetaldehyde, together with a substantial amount of acetic acid. The remainder of the liquid phase is primarily unconverted components of the initial charge. The hexamethylphosphoramide employed in this example is illustrative of a nitrogen-type promoter rather than of a phosphorous-type promoter because, in this compound, the phosphorous atom is in the +6 valence state and does not possess a pair of electrons available for formation of a coordinate bond with the noble metal catalyst.

EXAMPLE XVI

The procedure and equipment of Example I are employed using as initial charge 60 parts of methyl acetate, 1.6 parts of palladium diacetate, 10 parts of N,N-dicyclohexylmethylamine, and 20 parts of methyl iodide. Carbon monoxide and hydrogen are added in the same fashion and to the same pressure used in Example I. Reaction is continued for 17 hours at 135° C. Analysis of the reaction products by G.C. techniques indicates the reaction effluent to contain 14.6 wt. % ethylidene diacetate and 4.9 wt. % acetaldehyde, together with a substantial amount of acetic acid. The remainder of the liquid phase is primarily unconverted components of the initial charge.

EXAMPLE XVII

The procedure and equipment of Example I are employed using as initial charge 30 parts of dimethyl ether, 43 parts of methyl acetate, 2 parts of palladium dichloride, 10 parts of triphenyl phosphine, and 31 parts of methyl iodide. Carbon monoxide and hydrogen are added as in Example I except that the pressures used are 300 psig and 300 psig, respectively. Reaction is continued for 17 hours at 150° C. Analysis of the reaction products by G.C. techniques indicates the reaction effluent to contain 2 wt. % ethylidene diacetate and 44 wt. % methyl acetate, together with a substantial amount of acetic acid. The remainder of the liquid phase consists primarily of unconverted components of the initial charge.

EXAMPLE XVIII

The procedure and equipment of Example I are employed using as initial charge 60 parts of methyl acetate, 3 parts of chromium carbonyl, 3 parts of rhodium trichloride trihydrate, and 26 parts of N-methyl pyridinium iodide. Carbon monoxide and hydrogen are added as in Example I except that the pressures used are 300 psig and 300 psig, respectively. Reaction is continued for 17 hours at 150° C. Analysis of the reaction products by G.C. techniques indicates the reaction effluent to contain 41.2 wt. % ethylidene diacetate and 19 wt. % acetic anhydride, together with a substantial amount of acetic acid. The remainder of the liquid phase consists primarily of unconverted components of the initial charge.

EXAMPLE XIX

The procedure and equipment of Example I are employed using as initial charge 60 parts of methyl acetate, 3 parts of rhodium chloride trihydrate, and 20.5 parts of chromium iodide ($CrI_3$). Carbon monoxide and hydrogen are added as in Example I except that the pressures used are 300 psig and 300 psig, respectively. Reaction is continued for 17 hours at 150° C. Analysis of the reaction products by G.C. techniques indicates the reaction effluent to contain 5.2 wt. % ethylidene diacetate and 10 wt. % acetic anhydride, together with a substantial amount of acetic acid. The remainder of the liquid phase consists primarily of unconverted components of the initial charge.

Examples XVIII and XIX illustrate the flexibility of this process in relation to halide source since in neither example were any methyl halide, acetyl halide, or hydrogen halide charged. Example XVIII illustrates that organic halogen containing compounds are suitable halide sources, while Example XIX illustrates the use of inorganic materials as halide sources.

EXAMPLE XX

The procedure and equipment of Example I are employed using as initial charge 100 parts (mole basis) of methyl acetate, 17 parts (mole basis) of methyl iodide, 0.9 part (mole basis) of palladium acetate ($Pd(C_2H_5O_2)_2$), and 4 parts (mole basis) of benzotriazole. Carbon monoxide and hydrogen are added as in Example I except that the pressures used are 300 psig and 300 psig, respectively. Reaction is continued for 16 hours at 152° C. Analysis of the reaction products by G. C. techniques indicates the reaction effluent to contain 20 wt. % ethylidene diacetate, 2 wt. % acetic anhydride, 3 wt. % acetaldehyde, together with a substantial amount of acetic acid. The remainder of the liquid phase consists primarily of unconverted components of the initial charge.

That portion of the effluent obtained in this example which corresponds to the ethylidene diacetate adsorption peak during the gas chromatographic analysis is, upon desorption, passed through an ice-water trap in order to condense and recover the ethylidene diacetate. The ethylidene diacetate so obtained is analyzed by infra-red spectographic techniques and found to have an infra-red spectrum identical with that of a commerically-obtained sample of pure ethylidene diacetate, thus confirming the identity of the product and the validity of the gas chromatographic techniques used for analysis in this and in the other examples presented herein.

EXAMPLE XXI

Methyl acetate (100 parts), methyl iodide (36.6 parts), palladium acetate (3.5 parts), triphenyl phosphine (8 parts) and chromium carbonyl (24 parts) are charged into a glass lined pressure vessel which is pressured to 600 psig at room temperature with carbon monoxide and hydrogen (95:5 ratio) and the vessel is then closed and heated with stirring at 150° C. for 6 hours. Carbon monoxide and hydrogen mixture (95:5 ratio) is continuously supplied to maintain a continuous total pressure in the vessel of 1000 psig. After the 6 hours reaction time, G. C. analysis of the liquid phase shows it to contain 14.2 wt. % ethylidene diacetate, 19.1 wt. % methyl acetate, 59.8 wt. % acetic anhydride, and 6.9 wt. % acetic acid.

EXAMPLE XXII

Methyl acetate (100 parts), methyl iodide (27 parts), palladium acetate (2.6 parts), triphenyl phosphine (6 parts), and chromium carbonyl (17.9 parts) are charged into a glass lined pressure vessel which is pressured to 600 psig at room temperature with carbon monoxide and hydrogen (97.5:2.5 ratio) and the vessel is then closed and heated with stirring at 150° C. for 6 hours. Carbon monoxide and hydrogen mixture (97.5:2.5 ratio) is continuously supplied to maintain a continuous total pressure in the vessel of 1000 psig. After the 6 hours reaction time, G. C. analysis of the liquid phase shows it to contain 7.1 wt. % ethylidene diacetate, 24.9 wt. % methyl acetate, 63.8 wt. % acetic anhydride, and 4.2 wt. % acetic acid.

EXAMPLE XXIII

Methyl acetate (100 parts), methyl iodide (12.5 parts), chromium carbonyl (18 parts), triphenyl phosphine (5.5 parts) and palladium acetate (2.3 parts) are charged into a glass-lined pressure reactor with 750 psig of a gas mixture composed of 97.3% carbon monoxide and 2.7% hydrogen. The vessel is stirred for 14 hours at 150° C. G. C. analysis of the liquid phase shows it to contain 10% ethylidene diacetate, 18% methyl acetate, 68% acetic anhydride and 4% acetic acid.

EXAMPLE XXIV

Methyl acetate (100 parts), methyl iodide (12.5 parts), chromium carbonyl (18 parts), triphenyl phosphine (5.5 parts) and palladium acetate (2.3 parts) are charged into a glass-lined pressure reactor with 750 psig of a gas mixture composed of 98.7% carbon monoxide and 1.3% hydrogen. The vessel is stirred for 14 hours at 150° C. G. C. analysis of the liquid phase shows it to contain 7% ethylidene diacetate, 15% methyl acetate, 75% acetic anhydride, and 3% acetic acid.

EXAMPLE XXV

Methyl acetate (100 parts), methyl iodide (12.5 parts), chromium carbonyl (18 parts), triphenyl phosphine (5.5 parts) and palladium acetate (2.3 parts) are charged into a glass-lined pressure reactor with 750 psig of a gas mixture composed of 93.3% carbon monoxide and 6.7% hydrogen. The vessel is stirred for 3 hours at 150° C. G. C. analysis of the liquid phase shows it to contain 21% ethylidene diacetate, 38% methyl acetate, 29% acetic anhydride, and 12% acetic acid.

EXAMPLE XXVI

Methyl acetate (100 parts), methyl iodide (14 parts), palladium acetate (2.7 parts), triphenyl phosphine (6.2 parts) and chromium carbonyl (20.6 parts) are charged into a Hastelloy-C pressure vessel which is pressured to 600 psig at room temperature with carbon monoxide and hydrogen (3:1 ratio) and the vessel is then closed and heated with stirring at 150° C. for 9 hours. A carbon monoxide and hydrogen mixture is continuously supplied to maintain a continuous total pressure in the vessel of 900 psig and in amounts sufficient to keep the carbon monoxide to hydrogen ratio in the reaction at the 3:1 ratio. After the 9 hours reaction time, G. C. analysis of the liquid phase shows it to contain 42 wt. % ethylidene diacetate, 16 wt. % methyl acetate, 1 wt. % acetaldehyde, 23 wt. % acetic anhydride, and 18 wt. % acetic acid.

EXAMPLE XXVII

Methyl acetate (100 parts), methyl iodide (18.8 parts), acetic anhydride (34 parts), palladium acetate (3.6 parts), triphenyl phosphine (8 parts) and chromium triiodide (55 parts) are charged into a Hastelloy-C pressure vessel which is pressured to 600 psig at room temperature with carbon monoxide and hydrogen (2:1 ratio), and the vessel is then closed and heated with stirring at 160° C. for $2\frac{1}{2}$ hours. A carbon monoxide and hydrogen mixture (2:1 ratio) is continuously supplied to maintain a continuous total pressure in the vessel of 900 psig. After the $2\frac{1}{2}$ hours reaction time, G. C. analysis of the liquid phase shows it to contain 30 wt. % ethylidene diacetate, 33 wt. % methyl acetate, 0.3 wt. % acetaldehyde, 20 wt. % acetic anhydride, and 16.7 wt. % acetic acid.

EXAMPLE XXVIII

Methyl acetate (100 parts), methyl iodide (65 parts), palladium acetate (5.2 parts), triphenyl phosphine (7.9 parts), chromium carbonyl (9.5 parts) and ethylene glycol diacetate as solvent (130 parts) are charged into a Hastelloy-C pressure vessel which is pressured to 600 psig at room temperature with carbon monoxide and hydrogen (1:1 ratio). The vessel is then closed and heated with stirring at 150° C. for 10 hours. Carbon monoxide and hydrogen are continuously supplied to maintain a total pressure in the vessel of 850 psig and a ratio of carbon monoxide and hydrogen in the vessel of 1:1. After the 10 hours reaction time, G. C. analysis of the liquid phase shows it to contain 48.8 wt. % ethylidene diacetate, 0.6 wt. % acetaldehyde, 13 wt. % methyl acetate, 11.6 wt. % acetic anhydride, and 26 wt. % acetic acid.

EXAMPLE XXIX

Methyl acetate (100 parts), methyl iodide (34 parts), triphenyl phosphine, (17 parts) and palladium acetate (1.7 parts) are charged into a glass-lined pressure reactor with 1000 psig of a gas mixture composed of 70% carbon monoxide and 30% hydrogen. The vessel is stirred for 6 hours at 150° C. G.C. analysis of the liquid phase shows it to contain 33% ethylidene diacetate, 43% methyl acetate, 19% acetic acid, and 5% acetaldehyde.

It will be understood that modifications and variations in the details described above may be effected by those skilled in the art without departing from the spirit of this invention or from its scope as defined in the appended claims. Accordingly, it is intended that all matter contained in the foregoing description shall be interpreted as illustrative only and not in a limiting sense.

What is claimed is:

1. A process for the preparation of ethylidene diacetate which process comprises contacting (a) at least one member of the group consisting of methyl acetate and dimethyl ether, (b) carbon monoxide, and (c) hydrogen with a source of halide, the halide being at least one member of the group consisting of bromide and iodide, within a reaction zone under substantially anhydrous conditions in the presence of a catalyst consisting essentially of a Group VIII noble metal, or compound thereof, in the presence of a promoter which is at least one element having an atomic weight greater than 5 of Groups IA, IIA, IIIA, IVB, VIB the non-noble metals of Group VIII, the metals of the lanthanide series and the metals of the actinide series of the Periodic Table.

2. A process in accordance with claim 1 wherein the element has an atomic weight less than 100.

3. A process in accordance with claim 1 wherein the promoter is at least one metal of the group consisting of the metals of Group VIB and the non-noble metals of Group VIII.

4. A process in accordance with claim 3 wherein the promoter is selected from at least one member of the group consisting of chromium, cobalt, iron, and nickel.

5. A process in accordance with claim 4 wherein the promoter is chromium.

6. A process in accordance with claim 1 wherein the quantity of promoter is from 0.0001 mole to 100 moles per mole of Group VIII noble metal catalyst present within the reaction zone.

7. A process for the preparation of ethylidene diacetate which process comprises contacting, in the presence of a liquid phase reaction medium confined within a reaction zone, (a) at least one member of the group consisting of methyl acetate and dimethyl ether, (b) carbon monoxide, and (c) hydrogen with a source of halide, the halide being at least one member of the group consisting of bromide and iodide, said contacting being effected under substantially anhydrous conditions and in the presence of a carbonylation catalyst consisting essentially of a Group VIII noble metal or compound thereof, wherein the Group VIII noble metal is at least one member selected from the group of palladium and rhodium, and in the presence of a promoter which is at least one element having an atomic weight greater than 5 Groups IA, IIA, IIIA, IVB, VIB, the non-noble metals of Group VIII, the metals of the lanthanide series and the metals of the actinide series of the Periodic Table.

8. A process in accordance with claim 7 wherein the promoter is at least one metal of the group consisting of the metals of Group VIB and the non-noble metals of Group VIII.

9. A process in accordance with claim 8 wherein the promoter is selected from at least one member of the group consisting of chromium, cobalt, iron, and nickel.

10. A process in accordance with claim 9 wherein the promoter is chromium.

11. A process in accordance with claim 9 wherein the quantity of promoter is from 0.0001 mole to 100 moles per mole of Group VIII noble metal catalyst present within the reaction zone.

12. A process in accordance with claim 7 wherein the quantity of promoter is from 0.0001 mole to 100 moles per mole of Group VIII noble metal catalyst present within the reaction zone.

* * * * *